United States Patent [19]

Erlich et al.

[11] Patent Number: 5,314,809
[45] Date of Patent: May 24, 1994

[54] METHODS FOR NUCLEIC ACID AMPLIFICATION

[75] Inventors: Henry A. Erlich, Oakland; Russell G. Higuchi, San Francisco, both of Calif.

[73] Assignee: Hoffman-La Roche Inc., Nutley, N.J.

[21] Appl. No.: 33,072

[22] Filed: Mar. 10, 1993

Related U.S. Application Data

[63] Continuation of Ser. No. 718,576, Jun. 20, 1991, abandoned.

[51] Int. Cl.$^5$ .................. C12Q 1/68; C12P 19/34; C07H 15/12
[52] U.S. Cl. ..................... 435/91.2; 435/6; 536/24.3
[58] Field of Search ............. 435/6, 91; 536/24.3

[56] References Cited

U.S. PATENT DOCUMENTS

| | | | |
|---|---|---|---|
| 4,358,535 | 11/1982 | Falkow et al. | 435/5 |
| 4,582,789 | 4/1986 | Sheldon, III et al. | 435/6 |
| 4,683,195 | 7/1987 | Mullis et al. | 435/6 |
| 4,683,202 | 7/1987 | Mullis | 435/91 |
| 4,889,818 | 12/1989 | Gelfand et al. | 435/194 |
| 4,965,188 | 10/1990 | Mullis et al. | 435/6 |

OTHER PUBLICATIONS

G. M. Wahl et al., 1987, Methods in Enzymology 152, 399–407 "Molecular Hybridization of Immobilized Nucleic Acids: Theoretical Concepts and Practical Considerations".
S. Kwok and R. Higuchi, 1989, Nature 339:237–238, "Avoiding False Positives With PCR".
U. B. Gyllensten and H. A. Erlich, 1988, Proc. Natl. Acad. Sci. USA 85: 7652–7656, "Generation of Single-Stranded DNA by the Polymerase Chain Reaction and its Application to Direct Sequencing of the HLA-DQA Locus".
Kemp, et al., Colorimetric Detection of Specific DNA Segments Amplified by Polymerase Chain Reactions, Proc. Nat'l Acad. Sci. U.S.A. 86:2423–2427 (Apr. 1989).
Gonzalez-Cadavid et al., 1991, Chemical Abstracts 114(11):190, "Automated Direct Sequencing of Polymerase Chain Reaction-Amplified Fragments of the Human Ha-ras Gene".
Saiki et al, 1986, Nature 324:163–166, "Analysis of Enzymatically Amplified B-Globin and HLA-DQA DNA With Allele-Specific Oligonucleotide Probes".
Myers et al., 1989, PCR Technology, Ed. Erlich, Stockton Press, New York, "Mutation Detection by PCR, GC–Clamps, and Denaturing Gradient Gel Electrphoresis".
Scharf et al., 1989, Proc. Natl. Acad. Sci. USA 86:6215–6219, "Specific HLA-DQB and HLA-DRB1 Alleles Confer Susceptibility to Pemphigus Vulgaris".
Wu et al, 1989, Proc. Natl. Acad. Sci. USA 86:2757–2760, "Allele-Specific Enzymatic Amplification of B-Globin Genomic DNA for Diagnosis of Sickle Cell Anemia".
Li et al., 1990, Proc. Natl. Acad. Sci. USA 87:4580–4584, "Direct Electrophoretic Detection of the Allelic State of Single DNA Molecules in Human Sperm by Using the Polymerase Chain Reaction".
Wallace et al., 1979, Nuc. Acids Res. 6(11):3543–3557, "Hybridization of Synthetic Oligodeoxyribonucleotides to Phi Chi 174 DNA: the Effect of Single Base Pair Mismatch".
Breslauer et al., 1986, Proc. Natl. Sci. USA 83:3746–3750, "Predicting DNA Duplex Stability the Base Sequence".
Wu et al., 1991, DNA and Cell Biology 10(3):233–238, "The Effect of Temperature and Oligonucleotide Primer Length on the Specificity and Efficiency of Amplification by the Polymerase Chain Reaction".
Erlich et al., 1991, Science 252:1643–1651, "Recent Advances in the Polymerase Chain Reaction".
Kemp et al., Nov., 1990, Gene 94:223–228, "Simplified Colorimetric of Polymerase Chain Reactions: Detection of HIV Sequences in AIDS Patients".

*Primary Examiner*—Scott A. Chambers
*Attorney, Agent, or Firm*—George M. Gould; Patricia S. Rocha; Stacey R. Sias

[57] ABSTRACT

Methods are provided for enhanced specificity and sensitivity of nucleic acid amplification. The methods are simplified nested amplification procedures wherein both inner and outer primer pairs are present in the amplification reaction mixture. According to the methods, the thermocycling profile, as well as the sequences, length, and concentration of amplification primers, is modified to regulate which primers are annealed and extended on the target during any particular amplification cycle. The methods described are particularly suitable in PCR amplifications and have numerous applications in molecular biology, medical diagnostics, and forensics.

18 Claims, 4 Drawing Sheets

METHODS FOR NUCLEIC ACID AMPLIFICATION

This is a continuation of application Ser. No. 07/718,576; filed Jun. 20, 1991, which is abandoned.

FIELD OF THE INVENTION

The present invention provides improved methods and compositions for nucleic acid amplification. The novel methods provided offer enhanced target specificity, and sensitivity over prior methods and are particularly useful for amplification and detection of target sequences by the polymerase chain reaction (PCR). Specifically, according to the present invention, the thermocycling profile as well as the sequence, length, and concentration of amplification primers are modified to provide improved target specificity. The methods of the invention have numerous applications in the fields of molecular biology, medical diagnostics and forensics.

DESCRIPTION OF RELATED ART

The disclosed nucleic acid amplification methods and compositions offer the advantages of enhanced specificity and sensitivity over prior methods for amplifying nucleic acids. The methods relate to the use of modified thermocycling procedures for achieving improved amplification results. In one aspect of the invention, the methods also relate to the use of nested primers for increased specificity. The invention eliminates the disadvantages of prior nested priming procedures and reduces amplification artifacts such as primer-dimer. The improved amplification methods also enhance detection by increasing the amount of target-specific amplified product.

Methods for nucleic acid detection are generally accomplished using oligonucleotide probes. For example, Falkow et al., U.S. Pat. No. 4,358,535, disclose a method for detecting pathogens by spotting a sample (e.g., blood, cells, saliva, etc.) on a filter, lysing the cells, and fixing the DNA through chemical denaturation and heating. Then labelled DNA probes are added and allowed to hybridize with the fixed sample DNA. Hybridization indicates the presence of the pathogen's DNA.

The sensitivity and specificity of nucleic acid detection methods was greatly improved by the invention of the polymerase chain reaction (PCR). PCR is a process for amplifying nucleic acids and involves the use of two oligonucleotide primers, an agent for polymerization, a target nucleic acid template, and successive cycles of denaturation of nucleic acid and annealing and extension of the primers to produce a large number of copies of a particular nucleic acid segment. With this method, segments of single copy genomic DNA can be amplified more than 10 million fold with very high specificity and fidelity. PCR methods are disclosed in U.S. Pat. No. 4,683,202, which is incorporated herein by reference. Methods for detecting PCR products are particularly described in U.S. Pat. No. 4,683,195, which is incorporated herein by reference. Those methods require an oligonucleotide probe capable of hybridizing with the amplified target nucleic acid.

Sensitivity is critical when the amplification target is a rare sequence. The detection sensitivity is limited by the amount of amplified product available to be detected. Rare sequences, for example, AIDS virus nucleic acids in an AIDS positive but otherwise healthy individual, or a rare gene transcript indicative of oncogenesis, are very difficult to detect and can be overlooked in conventional analytical practices. Forensic samples often comprise minute amounts of nucleic acid or partially degraded DNA.

A difficulty in detecting a rare sequence is that there can be a high ratio of non-target to target sequence. The ability of a PCR to discriminate between target and non-target DNA and amplify only target sequences is a key aspect of improved sensitivity. Discrimination between non-target and target is a reflection of the specificity of the primers and reaction conditions. The more specific a reaction is the greater the relative amount of the specific target sequence that is produced and the easier that product is to detect. An increase in specificity can, therefore, increase sensitivity as well.

The need for improved sensitivity and specificity is addressed in U.S. Pat. No. 4,683,195, which describes the use of nested primers for increasing PCR sensitivity in the amplification of single copy genes. The procedure requires that following PCR the reaction mixture is diluted 10-fold to reduce the concentration of the first primer pair, and a second primer pair is introduced into the reaction mixture and PCR thermocycling is repeated. According to the method, the second primer pair is designed to be internal to the first primer pair to amplify a subsegment of the first PCR product. The method increases specific amplification, i.e., reduces non-specific background amplification products and therefore increases sensitivity. Such non-specific amplification products, although they arise by virtue of fortuitous partial homology to the flanking primers, are unlikely to also have sufficient homology to the nested primers to continue to amplify.

The two step reaction has several drawbacks resulting from the presence of the first primer pair in the second PCR, and the need for additional reagents, including enzyme, following the dilution of the first PCR mixture. The drawbacks of the nested priming method are compounded by the potential for cross contamination between samples during the dilution steps. Due to the enormous amplification possible with the PCR process, small levels of DNA carryover from samples with high DNA levels, positive control templates or targets from previous amplifications can result in PCR product, even in the absence of purposefully added template DNA. Particular methods and precautions for practicing PCR with a minimum of cross contamination are described in Higuchi and Kwok, 1989, *Nature* 339:237–238; Kwok and Orrego, Innis et al. eds 1990, *PCR Protocols: A Guide to Methods and Applications*, Academic Press, Inc., San Diego, Calif.; and copending U.S. Ser. No. 609,157, which are all incorporated herein by reference.

In general, alternative procedures for enhanced specificity involve modified product detection procedures. For example, Saiki et al., 1986, *Nature* 324:163–166, describe a method for detecting allelic sequence variations due to single-base substitutions in human genomic DNA. The publication provides allele-specific oligonucleotide (ASO) probes that will only anneal to sequences that perfectly match the probe; a single mismatch being sufficient to prevent hybridization. The ASO probes are used in conjunction with amplification of a target segment containing an allelic sequence of interest. This method is also described in copending patent application U.S. Ser. No. 347,495, filed May 4, 1989, which is incorporated herein by reference.

Modifications to the nested primer method disclosed in the '195 patent have been described. Kemp et al.

(1989, *Proc. Natl. Acad. Sci. USA* 86:2423-2437) describe a modified nested priming procedure wherein the internal primers are labeled for subsequent capture and detection. Li et al. (1990, *Proc. Natl. Acad. Sci. USA* 84:4580-4584) describe a "heminesting method" for allele-specific detection. The method requires amplification using a generic primer pair followed by a 1:50 dilution of the PCR product. The product is then reamplified using three nested, e.g., two upstream and one downstream, primers. For any particular allele only one nested primer is sufficiently complementary to the target to be extended. The primers differ in length, and the size of the PCR product allows the allelic state to be determined.

Wu et al. (1989, *Proc. Natl. Acad. Sci. USA* 86:2757-2760) describe a method for allele-specific amplification for diagnosing of sickle cell anemia. According to the method, three primers are included in the amplification reaction: two allele-specific primers; one specific for the sickle cell allele and one specific for the normal allele; and a third primer for amplifying either allele. Under stringent conditions, the allele-specific primer will only be extended on the complementary target. Accordingly, only one primer will only be extended on the complementary target. Accordingly, only one primer pair will function in PCR for any particular target. Scharf et al. (1989, *Proc. Natl. Acad. Sci. USA* 86:6215-6219) also describe allele-specific amplification. In a non-nested procedure, primer sequences were modified to distinguish several particular alleles by selective amplification.

An alternate method for detecting genetic polymorphisms is described in Myers et al., 1989, *PCR Technology*, Ed. Erlich, Stockton Press, New York. According to the method, PCR primers are modified to affect the denaturation profile of the amplified DNA when the product is electrophoresed through a denaturation gradient gel after amplification. The modified primers include G-C polynucleotide tails which are referred to as G-C clamps because of the effect of increased G-C content on the thermostability of a fragment.

Copending patent application U.S. Ser. No. 248,896, filed Sep. 23, 1988, and incorporated herein by reference, describes a method for generating single-stranded DNA for use in DNA sequencing reactions. According to the method, unequal molar amounts of two amplification primers are employed to produce an excess of one strand of the PCR product. The method is also described in Gyllensten and Erlich, 1988, *Proc. Natl. Acad. Sci. USA* 85(20): 7652-7656, which is incorporated herein by reference.

The desire to limit the possibility of cross contamination and simplify product detection by decreasing the number of manipulative steps for amplifying and detecting a target nucleic acid has been addressed in, for example, copending commonly assigned U.S. Ser. No. 563,758, filed Aug. 6, 1990, and incorporated herein by reference. U.S. Ser. No. 563,758 describes an alternative assay method for detecting amplified nucleic acids. The process employs the 5' to 3' exonuclease activity of a nucleic acid polymerase to cleave annealed labeled oligonucleotides from hybridized duplexes and release labeled oligonucleotide fragments for detection. The method is suitable for detecting PCR products and requires a primer pair and a labeled oligonucleotide probe having a blocked 3'-OH terminus to prevent extension by the polymerase.

There is a need for simplified methods for increasing both the specificity and sensitivity of nested primer amplification. Improved methods are desirable that also eliminate processing steps and minimize the opportunity for cross contamination and subsequent inaccurate results. The present invention meets these needs.

SUMMARY OF THE INVENTION

In one aspect, the present invention provides a method for nested amplification of a sequence within a target nucleic acid in a sample, the method comprises: (a) mixing the sample in an amplification reaction mixture containing an outer primer pair and an inner primer pair, wherein the outer primer pair is capable of amplifying a segment of the target nucleic acid to provide an amplified target sequence, and the inner primer pair is capable of amplifying a subsequence within the target sequence; (b) treating the amplification reaction mixture of step (a) in an amplification reaction at a temperature for annealing and extending the outer primer pair on the target nucleic acid and at a temperature for denaturing the extension products of the outer primer pair to provide an amplified target sequence, wherein the temperature for annealing and extending the outer primer pair is higher than the temperature for annealing and extending the inner primer pair to the target nucleic acid; and (c) treating the mixture of step (b) in an amplification reaction at a temperature for annealing and extending the inner primer pair on the amplified target sequence, and at a temperature for denaturing the extension products of the inner primer pair to provide an amplified subsequence.

In another embodiment of the method, at step (c), the temperature for denaturing the extension products of the inner primer pair is suitable for denaturing the extension products of the outer primer pair and the method further comprises: (d) amplifying the subsequence, at a temperature for annealing and extending the inner primer pair on the amplified target sequence, and at a temperature for denaturing only the extension products of the inner primer pair to provide an amplified subsequence, wherein the temperature for denaturing only the extension products of the inner primer pair is lower than the temperature for denaturing the extension products of the outer primer pair.

In another aspect, the invention provides a method of improved specificity in a PCR that comprises: (a) mixing a sample containing a target nucleic acid sequence in an amplification reaction mixture containing a primer pair for specifically amplifying the target; (b) amplifying the target sequence at a temperature for annealing and extending the primer pair that is between 1° C. and 10° C. higher than the Tm for the primer pair, and (c) amplifying the amplification reaction mixture of step (b) at a temperature for efficiently annealing and extending the primer pair to provide an amplified target sequence.

DETAILED DESCRIPTION OF THE INVENTION

Figure 1:
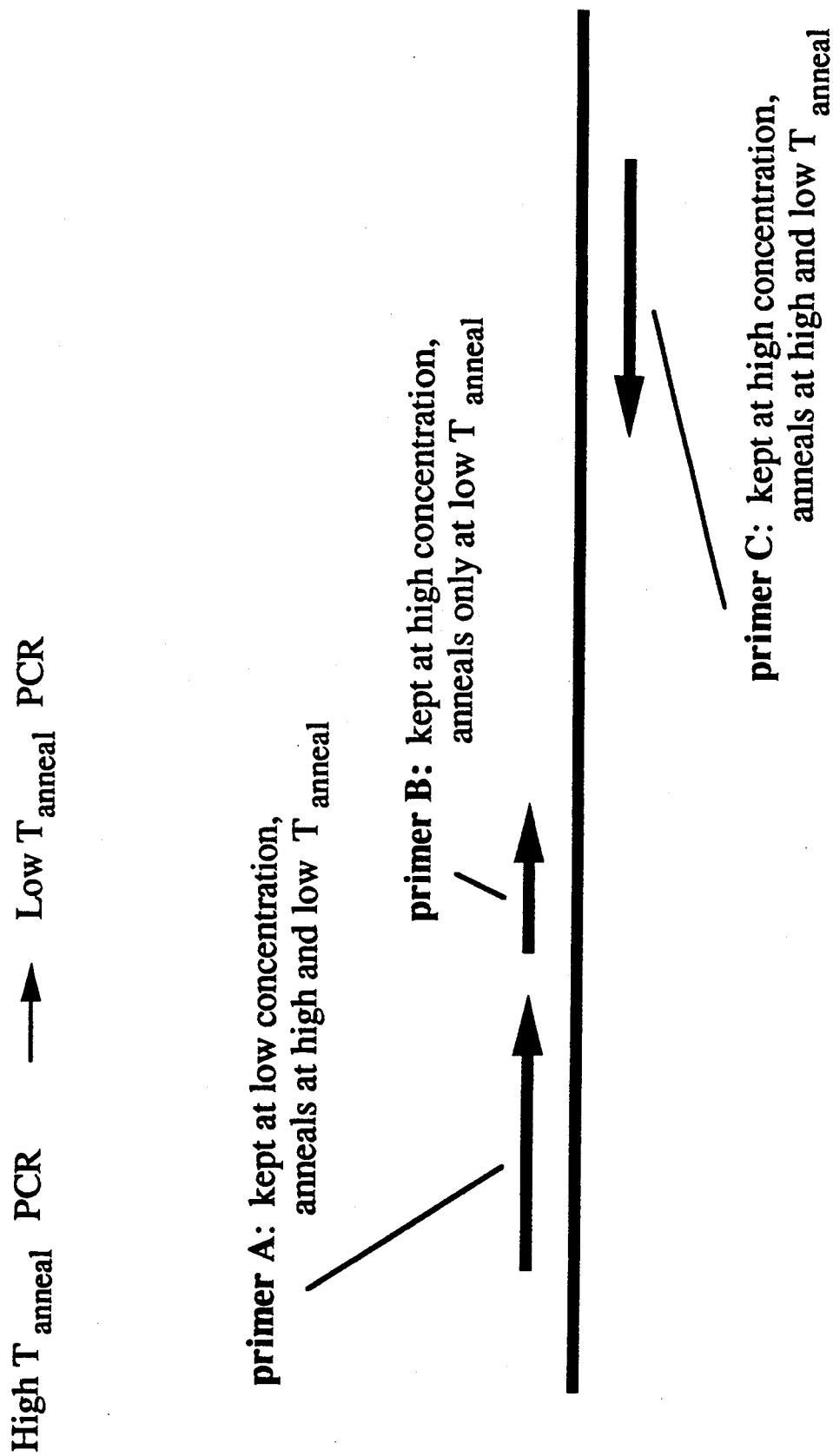
FIG. 1 provides a schematic description of "Drop-In" PCR.

The present invention provides improved methods for nested primer amplification. The methods offer improved specificity and sensitivity over prior methods. According to the invention, the thermocycling conditions of the amplification reaction are modified to provide improved results. The sequence, length, and/or concentration of amplification primers are modified as well. In addition, in one embodiment only two primers are required when the temperature cycling conditions are modified during amplification. Generally, however, the methods provide that more than two amplification primers are included in the amplification reaction mixture. The methods of the invention have fewer steps than prior nested amplification methods and consequently offer speed and simplicity over prior nested priming methods.

The methods are particularly suitable in PCR-based amplification techniques wherein a first and second primer are present in the reaction for amplifying a target nucleic acid. According to the invention, for improved nested amplification, a third primer capable of hybridizing to the amplification product generated by the first and second primers is included in the amplification reaction. The modified nested priming methods utilize the distinct properties of each primer in the amplification reaction mixture to control which primers are extended during each thermocycle. The methods are suitable for amplification of any particular target sequences. In a clinical setting, the methods offer speed, simplicity, and decreased opportunity for cross-contamination between samples by minimizing the number of manipulative steps of prior nested amplification methods.

The present methods are suitable for use in any nucleic acid amplification process that is characterized by primer extension and thermocycling. The embodiments of the invention provided herein are PCR-based methods, although the invention is not limited to PCR amplification. PCR is widely practiced in the arts that relate to the present invention and a brief summary of the generic PCR process is provided for convenience.

Amplification of DNA by PCR is disclosed in U.S. Pat. Nos. 4,683,195 and 4,683,202 (both of which are incorporated herein by reference). Methods for amplifying and detecting nucleic acids by PCR using a thermostable enzyme are disclosed in U.S. Pat. No. 4,965,188, which is incorporated herein by reference.

PCR amplification of DNA involves repeated cycles of heat-denaturing the DNA, annealing two oligonucleotide primers to sequences that flank the DNA segment to be amplified, and extending the annealed primers with DNA polymerase. The primers hybridize to opposite strands of the target sequence and are oriented so that DNA synthesis by the polymerase proceeds across the region between the primers, effectively doubling the amount of the DNA segment. Moreover, because the extension products are also complementary to and capable of binding primers, each successive cycle essentially doubles the amount of DNA synthesized in the previous cycle.

The term "amplification reaction system" refers to any in vitro means for multiplying the copies of a target sequence of nucleic acid. Such methods include but are not limited to polymerase (PCR), DNA ligase, (LCR), Qβ RNA replicase, and RNA transcription-based (TAS and 3SR) amplification systems.

The term "amplifying" which typically refers to an "exponential" increase in target nucleic acid is being used herein to describe both linear and exponential increases in the numbers of a select target sequence of nucleic acid.

The term "amplification reaction mixture" refers to an aqueous solution comprising the various reagents used to amplify a target nucleic acid. These include enzymes, aqueous buffers, salts, amplification primers, target nucleic acid, and nucleoside triphosphates. Depending upon the context, the mixture can be either a complete or incomplete amplification reaction mixture. The systems described herein are practiced routinely by those of skill in the relevant art. They have been described in detail by others.

This invention is not limited to any particular amplification system. As other systems are developed, those systems may benefit from the practice of this invention. A recent survey of amplification systems was published in Bio/Technology 8:290-293, April 1990, incorporated herein by reference. In addition to PCR, the ligase chain reaction (LCR) is an alternative thermocycling amplification procedure. A combined PCR/LCR procedure is suitable for use in conjunction with the present invention. A brief summary of the ligation chain reaction is provided below for the convenience of those not familiar with ligation based amplification systems and to provide an understanding of the breadth of the present invention.

LCR is described in PCT Patent Publication No. Wo 89/09835, which is incorporated herein by reference. The process involves the use of ligase to join oligonucleotide segments that anneal to the target nucleic acid. LCR results in amplification of an original target molecule and can provide millions of copies of product DNA. Consequently, the LCR results in a net increase in double-stranded DNA. The present detection methods are applicable to LCR as well as PCR. LCR requires an oligonucleotide probe for detecting the product DNA.

In the disclosed embodiment, Taq DNA polymerase is preferred although this is not an essential aspect of the invention. Taq polymerase, a thermostable polymerase, is active at high temperatures. Methods for the preparation of Taq are disclosed in U.S. Pat. No. 4,889,818 and incorporated herein by reference. Taq polymerase is available from Perkin-Elmer Cetus Instruments as a recombinant product or purified from *Thermus aquaticus*. However, other thermostable DNA polymerases isolated from Thermus species or non Thermus species (e.g., *Thermus thermophilous* or *Thermotoga maritima*), as well as non-thermostable DNA polymerase such as T4 DNA polymerase, T7 DNA polymerase, *E. coli* DNA polymerase I, or the Klenow fragment of *E. coli*, can also be used in PCR. The nucleic-5'-triphosphates utilized in the extension process, typically dATP, dCTP, dGTP, and dTTP, are present in total concentration typically ranging from 400 μM to 4.0 mM during the extension reaction, although preferably the concentration is between 500 μM and 1.5 mM.

Taq polymerase can be prepared as both a 94 kDa and a 62 kDa enzyme. The 62 kDa enzyme is a processed form of the 94 kDa enzyme resulting from proteolytic cleavage of the N-terminal region. Either form of the enzyme will function as an agent of polymerization in PCR. In addition to the N-terminal deletion, individual amino acid residues may be modified by oxidation, reduction, or other derivatization, or the protein may be cleaved to obtain fragments that retain activity.

Thus, modification to the primary structure itself by deletion, addition, or alteration of the amino acids incorporated into the sequence during translation can be made without destroying the high temperature DNA polymerase activity of the protein. Such substitutions or other alterations result in proteins useful in the methods of the present invention.

The availability of DNA encoding these sequences provides the opportunity to modify the codon sequence to generate mutant protein forms also having thermostable polymerase activity. For example, the amino acid and nucleic acid sequences Tth, the DNA polymerase of *Thermus thermophilus*, and Tma, the DNA polymerase of *Thermotoga maritima*, are provided by copending U.S. patent applications Ser. Nos. 455,967, filed Dec. 22, 1989, and 567,244, filed Aug. 13, 1990, which are incorporated herein by reference. The amino acid domains for various enzyme activities, including the 3' to 5' exonuclease activity (which is lacking in Taq and Tth), as well as the 5' to 3' exonuclease activity are described. Accordingly, domain shuffling or construction of chimeric DNA polymerases are used to provide thermostable DNA polymerases containing novel properties. Higuchi, 1989, in Erlich, *PCR Technology*, supra, which is incorporated herein by reference, describes "overlap" PCR for constructing novel gene sequences.

In one aspect of the present invention, a thermostable DNA polymerase that lacks 5' to 3' exonuclease activity is suitable. During extension of an outer primer, an inner primer, complementary to the same template strand, momentarily annealing to its target, is possibly degraded by the 5' to 3' exonuclease of activity of the wild-type DNA polymerase. The net effect of such degradation would be a decrease in the concentration of the inner primer. According to the invention, the inner primer is present in excess; therefore, the use of an enzyme lacking 5' to 3' exonuclease activity is not essential for practicing the present invention. However, the elimination or reduction of 5' to 3' exonuclease activity by, for example, site specific mutagenesis or deletion mutagenesis, provides an alternative form of thermostable polymerase for practicing the disclosed methods of amplification.

Methods for preparing thermostable DNA polymerases lacking 5' to 3' exonuclease activity are described in copending commonly assigned Ser. Nos. 567,244, filed Aug. 13, 1990; 455,967, filed Dec. 22, 1989; 590,213, filed Sep. 28, 1990; 590,490, filed Sep. 28, 1990; 590,466, filed Sep. 28, 1990; PCT/US90/07,641, filed Dec. 20, 1990; and U.S. Pat. No. 4,889,818, which applications and patent are incorporated herein by reference. In addition, the 62 kDa form of Taq polymerase is commercially available from Perkin Elmer Cetus Instruments as the Stoffel fragment of Taq polymerase, which lacks 5' to 3' exonuclease activity.

The term "oligonucleotide" as used herein is defined as a molecule comprised of two or more deoxyribonucleotides or ribonucleotides, preferably more than three, and usually more than ten. The exact size will depend on many factors, which in turn depends on the ultimate function or use of the oligonucleotide. The oligonucleotide may be derived synthetically or by cloning.

The term "primer" as used herein refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is initiated, i.e., in the presence of four different nucleoside triphosphates and a DNA polymerase in an appropriate buffer ("buffer" includes pH, ionic strength, cofactors, etc.) and at a suitable temperature.

The term "thermocycling profile" as used herein refers to the selected temperature parameters selected for "n" cycles of PCR. The thermocycling profile includes at least two temperatures, a high denaturation temperature, adequate for sample-template, and subsequent product, denaturation, and a low temperature appropriate for primer annealing and polymerase extension. Accordingly, in the present invention, particular thermocycling parameters are selected to control primer annealing and product denaturation and thus regulate accessibility and primer extension.

The choice of primers for use in PCR determines the specificity of the amplification reaction. Primers used in the present invention are generally oligonucleotides, usually deoxyribonucleotides several nucleotides in length, that can be extended in a template-specific manner by the polymerase chain reaction. The primer is sufficiently long to prime the synthesis of extension products in the presence of the agent for polymerization and typically contains 10-30 nucleotides, although that exact number is not critical to the successful application of the method.

In one aspect of the invention, short primers which generally require cooler temperatures to form sufficiently stable hybrid complexes with the template are provided to facilitate, via manipulation of the annealing temperature during thermocycling, the beginning of the nested primer phase of the amplification which ultimately enhances sensitivity and specificity of the amplification reaction. As used herein, short primers are characterized as less thermally stable when annealed to target DNA than flanking outer primers. Accordingly, short primers are generally 8-18. In another aspect of the invention, long primers containing a non-complementary tail, adding 20-100 nucleotides to the 10-30 nucleotide homologous primer region, are provided. The non-complementary regions are useful for providing extension products of increased thermostability which require higher temperatures for subsequent denaturation to serve as amplification templates.

Synthetic oligonucleotides can be prepared using the triester method of Matteucci et al., 1981, *J. Am. Chem. Soc.* 103:3185-3191. Alternatively automated synthesis may be preferred, for example, on a Biosearch 8700 DNA Synthesizer using cyanoethyl phosphoramidite chemistry.

A primer is selected to be "substantially" complementary to a strand of the template having a specific sequence. For primer extension to occur, the primer must be sufficiently complementary to anneal to the nucleic acid template under the reaction conditions. Not every nucleotide of the primer must anneal to the template for primer extension to occur. The primer sequence need not reflect the exact sequence of the template. For example, in one embodiment of the invention, a non-complementary nucleotide fragment or tail is attached to the 5' end of the primer with the remainder of the primer sequence being complementary to the template. Alternatively, non-complementary bases can be interspersed into the primer, provided that the primer sequence has sufficient complementarily with the template for hybridization to occur and allow synthesis of complementary DNA strand.

The choice of the specific nucleic acid target region to be amplified dictates primer sequence and amplification specificity. For example, primers to conserved regions may amplify a class of gene sequences, while primers complementary to variable regions confer greater product specificity. Scharf et al., 1989, *Proc. Natl. Acad. Sci. USA* 86:6215–6219, which is incorporated herein by reference, describe a method for allele specific amplification that requires two primer pairs. The first primer pair is generic for a class of sequences, i.e., HLA DR$\beta$, the second primer pair is specific for the DRw6 DR$\beta$1 allele. The primer pairs are used separately, and the results are compared. Consequently, amplification by the generic primer pair provides a positive control for discerning a negative result from a failed PCR.

The present invention is particularly suitable for allele-specific amplification and is improved over methods such as the Scharf et al. procedure described above. In one embodiment of the invention, the outer primers function as generic primers, and the inner primer, or primers, are allele specific. According to the present method, the outer primers generate a PCR product which then serves as a template to generate a second smaller PCR product. Thus, the detection of the larger, generic PCR product, specified by the outer primers, provides an internal positive control. The allele-specific amplification product is generated in the same reaction vessel without opening the tube. This advantage is also particularly significant in clinical screening where thousands of samples are simultaneously screened for the presence of a rare agent, such as the AIDS virus nucleic acids or in forensic analyses where a sample is archival or provides evidence of a crime and the amount of sample is extremely limited.

Amplification systems such as PCR require a target nucleic acid in a buffer compatible with the enzymes used to amplify the target. The target nucleic acid can be isolated from any source of biological materials including tissues, body fluids, feces, sputum, saliva, plant cells, bacterial cultures, and the like.

To amplify a target nucleic acid sequence in a sample, the sequence must be accessible to the components of the amplification system. In general, this accessibility is ensured by isolating the nucleic acids from a crude biological sample. A variety of techniques for extracting nucleic acids from biological samples are known in the art. For example, see those described in Maniatis et al., *Molecular Cloning: A Laboratory Manual* (New York, Cold Spring Harbor Laboratory, 1982); Arrand, Preparation of Nucleic Acid Probes, in pages 18–30, *Nucleic Acid Hybridization: A Practical* Approach (Eds. Hames and Higgins, IRL Press, 1985); or in *PCR Protocols*, Chapters 18–20 (Innis et al., Ed., Academic Press, 1990).

In general, the nucleic acid in the sample will be a sequence of DNA, most usually genomic DNA. However, the present invention can also be practiced with other nucleic acids, such as messenger RNA, ribosomal RNA, viral RNA, or cloned DNA. Suitable nucleic acid samples include single or double-stranded DNA or RNA for use in the present invention. Those of skill in the art will recognize that whatever the nature of the nucleic acid, the nucleic acid can be amplified merely by making appropriate and well recognized modifications to the method being used.

Those skilled in the art will know that the PCR process is mostly usually carried out as an automated process with a thermostable enzyme. In this process, the reaction mixture is cycled through a denaturing temperature range, a primer annealing temperature range, and an extension temperature range. Generally, the annealing and extension temperature ranges overlap, and consequently, PCR is often practiced as a two step cycling reaction comprising a denaturing step and an annealing-/extension step. A machine specifically adapted for use with a thermostable enzyme is disclosed more completely in EP No. 236,069 and is commercially available from Perkin Elmer Cetus Instruments, Norwalk, Conn., which is incorporated herein by reference.

In the process described herein, a sample is provided which contains, or is suspected of containing, a particular oligonucleotide sequence of interest, the "target nucleic acid". The target may be RNA or DNA or an RNA/DNA hybrid. The target may be single-stranded or double-stranded. Target preparation will be carried out in a manner appropriate for the particular amplification process to be implemented. For example, in a PCR method where the target nucleic acid is single-stranded, such as mRNA, the target may be first reverse transcribed into cDNA, prior to amplification.

Methods for reverse transcribing RNA into cDNA are well known and described in Maniatis et al., supra. Alternatively, preferred methods for reverse transcription utilize thermoactive DNA polymerases. These methods are described in commonly assigned, copending U.S. Ser. No. 455,611, filed Dec. 22, 1989 and incorporated herein by reference. U.S. Ser. No. 455,611 describes a procedure for coupled reverse transcription-/amplification of an RNA template using a thermostable DNA polymerase.

Detection of the amplified products can be accomplished by a number of known means. Such means include, but are not limited to, hybridization with isotopic or non-isotopically labeled probes in, for example, a dot blot or electrophoretic format. A detection format system may include a capture step, such as a solid support substrate and avidin-biotin label system (see, for example, copending U.S. Ser. No. 690,720, filed Apr. 24, 1991, which is incorporated herein by reference). European Patent Publication No. 237,362 also describes a PCR-based detection method termed "reverse" dot-blot in which the probe, instead of the amplified DNA, is fixed to the membrane. According to the method, the target, rather than the probe, is labeled for hybridization.

There are a number of ways to determine whether a probe has hybridized to a DNA sequence contained in a sample. Typically, the probe is labeled in a detectable manner. The target DNA (i.e., the amplified DNA in the PCR-reaction buffer) is bound to a solid support, and determination of whether hybridization has occurred involves determining whether the label is present on the solid support. This procedure can be varied, however, and is possible when the target is labeled and the probe is bound to the solid support. See, for example, copending Ser. No. 347,495, filed May 4, 1989, which is incorporated herein by reference.

Many methods for labeling nucleic acids, whether probe or target, are known in the art and are suitable for purposes of the present invention. Suitable labels may provide signals detectable by fluorescence, radioactivity, colorimetry, X-ray diffraction or absorption, magnetism, enzymatic activity, and the like. Suitable labels include fluoruphores, chromophores, radioactive isotopes (particularly $^{32}P$ and $^{125}I$), electrondense reagents, enzymes and ligands having specific binding partners. Enzymes are typically detected by their activity. For example, horse-radish-peroxidase (HRP) can be detected by its ability to convert diaminobenzidine to a blue pigment. A preferred method for HRP-based detection uses tetramethyl-benzidine (TMB) as described in *Clin. Chem.* 33:1368 (1987). An alternative detection system is the Enhanced Chemiluminescent (ECL) detection kit commercially available from Amersham. The kit is used in accordance with the manufacturer's directions.

Copending U.S. Ser. No. 695,201, filed May 2, 1991, is incorporated herein by reference and describes a method for detecting amplified nucleic acids without the use of a probe. The homogeneous assay system requires that amplification occurs in the presence of a detectable DNA binding agent, for example, ethidium bromide. The fluorescence of the amplification mixture increases as the target is amplified and the amount of double-stranded DNA present in the reaction mixture increases. The present invention is particularly suitable for use in conjunction with the homogeneous assay method disclosed in U.S. Ser. No. 695,201. The combined method is described in Example II and provides tremendous advantages over prior methods for amplifying and detecting nucleic acids.

The homogeneous assay method offers means for detecting the presence of target without opening the reaction vessel once the reaction is initiated. The present invention provides a method for nested amplification, also without opening the reaction vessel. Thus, according to the present invention, the combined method has the enhanced sensitivity and specificity of nested priming and the ease of detection of the homogeneous assay system. Without opening the reaction vessel, a sequence as rare as one copy in 70,000 cells can be detected without the additional processing or manipulative steps usually required for target detection. The possibility of cross contamination is greatly minimized by the invention. In another embodiment, the use of a spectrafluometer allows quantitation of the amount of product generated. Consequently, when used in a homogeneous assay, the present invention permits quantitative analysis for monitoring the progress of, for example, an infection or response to treatment regimen.

Commonly assigned, copending U.S. Ser. No. 609,157, filed Nov. 2, 1990, and incorporated herein by reference, describes improved methods for reducing the effects of cross-contamination of amplification reactions. The methods require the introduction of unconventional bases into the amplified product and exposing carryover to enzymatic and/or physical chemical treatment which effectively render the product incapable of serving as a template for subsequent amplifications. The nested amplification methods described herein are particularly suitable in conjunction with the sterilization methods described in U.S. Ser. No. 609,157. These methods enhance the sensitivity and reliability of amplification results by eliminating steps required in prior nested amplification methods and thereby minimizing product handling, which reduces carryover. The sterilization method provides additional assurance that contamination arising from carryover template are eliminated.

In general, it is preferred but not essential that the DNA polymerase is added to the PCR reaction mixture after both the primer and template are added. Alteratively, for example, the enzyme and primer are added last or the PCR buffer or template plus buffer are added last. It is generally desirable that at least one component that is essential for polymerization not be present until such time as the primer and template are both present, and the enzyme can bind to and extend the desired primer/template substrate (see U.S. Ser. No. 481,501, filed Feb. 16, 1990, which is incorporated herein by reference). This method, termed "hot start," improves specificity and minimizes the formation of "primer-dimer."

"Primer-dimer" refers to a double-stranded PCR product consisting of two PCR primers and their complementary sequences. The synthesis of primer-dimer results from the extension of one primer using the other primer as template. Primer-dimer can occur in the absence of target and appears to be a function of primer concentration. The initial formation of "primer-dimer" can occur at low temperatures (i.e., room temperature); "hot start" eliminates this phase of the thermal profile. Once formed, this PCR artifact is amplified very efficiently and is detected in reactions with rare, or no specific template. In rare template reactions, the primer-dimer can compete with the target fragment for primers and enzyme and prevent efficient target amplification.

The use of nested primers serves to decrease primer-dimer and enhance PCR specificity. U.S. Pat. No. 4,683,195 describes that the nested primer procedure requires two primer pairs. According to the method a first "outer" primer pair is used to amplify a target sequence and a second "inner" primer pair is used to amplify a subsegment of the PCR product formed from the first amplification reaction. According to the method described in the '195 patent, the reaction mixture is diluted 10-fold to reduce the concentration of the first primer pair after PCR, then the second primer pair is introduced into the reaction mixture. This method requires a number of additional steps, including, stopping the PCR, opening the reaction tube, diluting the reaction to eliminate or decrease the concentration of outer primers, adding a second primer pair, consequently adjusting buffer conditions, providing additional enzyme, and a second thermocycling reaction. These steps are eliminated by the present invention.

The present invention provides nested amplification methods and compositions wherein the outer and inner primers are all present in the initial reaction mixture, and the thermocycler is programmed to allow the outer primers, but not the inner primers, to amplify initially, and then to allow the inner primers, but not the outer primers, to amplify the targeted subsequence within the initial PCR product. The examples of the invention serve to illustrate that primers prepared according to the invention are made to "drop in" or "drop out" of the amplification reaction in accord with the desired result. In several embodiments, one member of the initial flanking i.e., outer, primer pair also functions as an inner or secondary primer. Consequently, only three primers are utilized. Alternatively, four individual primers are used, comprising both inner and outer primer pairs. When four primers are employed, either one or both of the inner primers are made to "drop-in."

According to the present invention, a third primer, internal to one member of the outer primers is included in a PCR reaction for amplifying a particular target segment. As the temperature in the PCR reaction is raised, a point is reached at which this third primer no longer stably anneals to the target template, while the flanking primers continue to stably anneal. Thus, the third primer has an optimum, annealing temperature for PCR, that is lower than the optimum annealing temperature of the flanking outer primer. This property can be imparted to the third primer by virtue of a shorter length and/or lower G-C content. Adjusting the annealing temperature during the amplification reaction determines which primer pair is extended by the polymerase during any particular annealing/extension cycle.

In one embodiment of the invention, the primer flanking the third primer is present at a low concentration. For the first nPCR cycles, the temperature during the extension phase of each PCR cycle is maintained sufficiently high, e.g., approximately 65° C. to prevent the short, inner primer(s) from annealing specifically and initiating amplification. The outer primers anneal sufficiently such that PCR proceeds normally at the high extension temperature. Prior to amplification plateau, when the supply of limiting outer primer is almost exhausted, the annealing temperature is decreased, for example, to approximately 42° C. At this temperature, the third primer "drops in" and proceeds to amplify the target for the remaining cycles. This procedure is schematically described in FIG. 1 and referred to herein as "drop-in" PCR. According to the figure, the outer primer pair comprises primers "A" and "C," the inner primer pair comprises primers "B" and "C," and primer "B" is the third primer.

Wu et al., 1991, *DNA and Cell Biology* 10(3):233–238, which is incorporated herein by reference, provides a formula for estimating the optimum annealing temperature for PCR for any particular primer/template duplex. The nearest neighbor thermodynamic data of Breslauer et al., 1986, *Proc. Natl. Acad. Sci.* 83:3746–3750, as well as methods described in Wallace et al., 1979, *Nuc. Acids Res.* 6:3543–3557, which are incorporated herein by reference, exemplify empirical formula for estimating Tm. Although Tm is generally slightly higher than the optimum annealing temperature for PCR, calculating Tm provides a guidance for one of ordinary skill in the art to empirically determine suitable temperatures for practicing the present invention.

For some targets, for example, HIV proviral DNA in a fixed amount of peripheral blood from HIV infected individuals, the amount of target present in a sample varies up to 1,000-fold. Drop-in PCR is particularly suitable for such an analysis because of the effect of limited outer primer concentration on the amplifications. In a particular sample, if the amount of target is high, the PCR reaches plateau quickly but not completely. If the amount of target in a sample is low, amplification continues. Consequently, using a limiting outer primer concentration, different reactions are brought to about the same state of limited amplification before the thermocycling conditions are altered to allow the nested primer to "drop-in." As a result, the effect of sample to sample variance on nested amplification results is diminished.

In an alternative embodiment for nested primer amplification, the need for a low concentration of one flanking primer is eliminated. According to the method, a high denaturation temperature and a high annealing temperature allow the outer primers, but not the inner primers, to be extended. A flanking primer is synthesized with a G-C rich tail. Because the non-complementary primer tail sequence is incorporated into the PCR product after two cycles of amplification, the G-C tails serves to raise the temperature necessary for denaturing the PCR product because of the increased thermostability of G-C pairs versus A-T pairs (see Myers et al., 1989, in *PCR Technology* ed. Erlich, Stockton Press, New York, which is incorporated herein by reference). The resulting difference in the denaturing temperature of the nested and flanking PCR products is then exploited to effectively shut down amplification from the tailed outer primer.

Once PCR product is made from the outer primers, and after the nested primers have been allowed to "drop-in" by manipulating the annealing temperature to initiate synthesis from the nested primer when desired, the denaturation temperature is lowered, i.e., from 96° C. to 86° C. At the lower temperature the outer primer PCR product does not completely denature and consequently cannot serve as a template. However, the lower denaturation temperature is sufficient to allow amplification of the nested PCR product. This aspect of the invention is summarized as follows. After n cycles, the annealing temperature is dropped, allowing the inner primers to anneal. After n+x cycles, the denaturation temperature is dropped, preventing the initial PCR product from denaturing and serving as a template for the outer primer. This strategy, termed "Drop-in/Drop-out" PCR can be practiced using only one internal primer as described in Examples I and II. In those embodiments, one flanking primer serves as both inner and outer primer and is unaffected by the altered thermal profile of the cycling reaction. Drop-in/Drop-out PCR is schematically described in FIG. 2.

One of ordinary skill in the art can readily use empirical means to determine the appropriate denaturation and annealing temperatures for any particular amplification reaction mixture and program a thermocycler accordingly. The drop-in/drop-out PCR method provides means for including high concentrations of all primers which is preferred for optimizing PCR efficiency while controlling which particular primer pair is extended at any cycle during the reaction. This aspect of the method for nested primer amplification is demonstrated in Examples I and II.

The Drop-in PCR method requires that a first outer primer is present at a low concentration. Generally, amplification primers are present at a concentration of 1–100 pmole per 100 $\mu$l reaction. For drop-in PCR a suitable concentration for the limited out primer is within the range of 1% to 50% of the concentration of second and third primers (i.e., the inner primer pair). As amplification proceeds, the amount of first primer becomes limiting, with respect to the other primers. Consequently, when the annealing temperature is decreased to the Tm of the third primer, annealing and extension of the inner primer is favored and the smaller primer PCR product begins to accumulate.

According to the invention, the change in the thermocycling profile during PCR enhances amplification specificity. As PCR proceeds, the non-specific primer events lead to a build up of non-target, i.e., background products. Once a thermocycle, using a non-target template, is complete, that template will continue to be amplified in successive cycles. Although outer primers anneal to the amplified non-target template, the inner primer does not. Each change in the thermocycling profile results in a change in the population of non-target template molecules. Therefore, with each change in the cycling parameters, the non-target amplification possible during the previous thermocycle is diminished, and consequently, target specificity is enhanced.

The number of cycles necessary at each thermocycling profile, or phase, is empirically determined and varies depending on the complexity of the sample, the particular target, and the relative amounts of target and background nucleic acid. The number of cycles required at the high annealing temperature, wherein the outer primers are extended, is one, or any number of cycles greater than one. It may be desirable to include, for example, 1-30 cycles at high annealing temperature, and the specific number of cycles is determined according to the particularities of the assay; i.e., sample, target, primers, and the specific result required.

It may be desirable to amplify a first PCR target using outer primers, for a number of cycles sufficient to provide a detectable signal. Using the homogeneous assay described in copending U.S. Ser. No. 695,201, the presence of the amplified product is readily determined by fluorescence, without opening the reaction vessel. The outer primers may be suitable for amplifying a region of interest known to be present such as a particular gene segment. Amplification of, for example, a genetic marker by an outer primer pair provides an internal positive control for indicating that amplification has occurred.

Subsequently, the thermocycling profile is altered, and the inner target or specific primers are utilized. The additional increase in PCR product determined by a further increase in fluorescence indicates the presence of a particular target sequence. However, detection of the outer primer pair amplification product is not an essential aspect of the invention. Amplification by the first (outer) primer pair serves to increase the number of target molecules providing additional templates for amplification by the second (inner) primer pair.

The second cycling phase in the Drop-in/Drop-out method (high T denaturation, low T anneal) serves to initiate amplification using the internal primers and provides target for the third cycling phase (low T denaturation, low T anneal). During the third cycling phase, the lowered denaturation temperature effectively eliminates outer primer amplification, while inner primer amplification continues. Amplification at high T denaturation and low T anneal converts outer PCR product to inner PCR template. In practice 1-10 cycles are sufficient for the second phase of the reaction, although more cycles may be desirable for a particular target.

The annealing temperature for any specific primer in PCR is a function of the % GC content of the oligonucleotide. Breslauer et al. supra, Wu et al. supra, and Wallace et al. supra provide empirical formula for determining annealing temperatures. It will be obvious to one of skill in the art to determine the annealing temperature suitable for any particular target and primer using the guidance provided by the present examples of the invention. The difference in the annealing temperature of the low T anneal and high T anneal cycles is at least 1° C. and preferably is 3° C.-30° C. Similarly, the primer extension temperature is readily determined by one of ordinary skill in the art using the cited references and the present examples as a guide.

The variation from high T denaturation to low T denaturation is as much as 20° C. or as little as 1° C. depending on the target and sample complexity, G-C content, and primer sequence. The shift to a low denaturation temperature prevents denaturation of non-target amplified DNA. Because this nucleic acid is non-target, the length and % GC content cannot be determined for estimating the optimum temperature for preventing denaturation. Consequently, the denaturation temperature is empirically determined using the present specification and examples as a guide. Myers et al. (1989, in Erlich et al. *PCR Technology* Stockton Press) is incorporated herein by reference and describes the effects of nucleotide sequences on the Tm of DNA subsegments or domains within a larger nucleic acid sequence. For example, a tailed primer comprising approximately 40 nucleotides of 100% GC is sufficient to alter the temperature required for complete denaturation of an amplified sequence 500 base pairs in length. Preferably, the G-C tail, added to the 5' end of the flanking primer is between 10 and 100 nucleotides in length.

In an additional aspect of the invention, a flanking primer is not required for enhanced product specificity. Following the protocol for Drop-in amplification using only the inner primer pair provides an unexpectedly superior result when compared to the results of amplification using standard PCR conditions. Example II clearly demonstrates this aspect of the invention.

Prior to the present invention, it was not known that amplification specificity is improved by subjecting the sample to at least one thermocycle using an annealing temperature higher than the Tm. The cycling profile is subsequently adjusted and the annealing temperature is lowered to the appropriate Tm. Thus, in one embodiment of the invention the temperature for primer annealing and extension is 1° C.-10° C. higher than the estimated Tm for the particular primer pair. Although amplification at this temperature is extremely inefficient, any primer extension that occurs is target specific. Consequently, during the high temperature cycle(s), the sample is enriched for the particular target sequence and any number of cycles, i.e., 1-15 enhances product specificity. The annealing temperature is then decreased to increase amplification efficiency and provide a detectable amount of PCR product.

This method is particularly useful for increasing sensitivity as well as specificity. For example, detection of AIDS virus nucleic acids present as 1 copy per 70,000 cells is enhanced by the method and is illustrated in Example I. Similarly, allele-specific amplification for detecting the presence of a one-base pair change is also improved by the addition of the high temperature annealing cycle(s).

In another aspect, the invention may be commercialized providing kits for enhanced amplification specificity. Kits would include inner and outer primer pairs for a specific target or allele. Kits may also include any of the following reagents for amplification such as a DNA polymerase, buffers, dNTPs, and a positive control template.

The examples provided herein offer general guidance for practicing the present invention and are not intended as a limitation to the scope of the invention.

EXAMPLE I

Drop-In/Drop-Out PCR: Detection of a Rare Target in the Presence of a High Background of Double-Stranded DNA The drop-in/drop-out amplification method was used for amplifying a rare single copy sequence in a background of DNA from 70,000 human cells. A modified nested primer procedure, as briefly described in the "Detailed Description" section as a primer "drop-in/drop-out" procedure, was designed to enhance PCR specificity. This assay was done as follows: into PCR reaction vessels 1 through 8 were aliquoted 50 microliters of solution, each containing 50 mM KCl; 10 mM TrisHCl, pH 8.3; 2.5 mM MgCl$_2$; 600 $\mu$M total dNTPs; 1.25 unit of Taq DNA polymerase (PECI); 1.27 $\mu$M ethidium bromide; 0.5 $\mu$g of human cell-line DNA; the primer pair RH171 (SEQ ID NO: 1) and RH176 (SEQ ID NO: 2), each primer at 0.2 $\mu$M; and the nested primer RH182 (SEQ ID NO: 3) also at 0.2 $\mu$M. A drop of mineral oil was used to cover the eight solutions in order to prevent evaporation. Primer RH176 (SEQ ID NO: 2) carries a GC-rich, non-homologous (to target sequence), 5' "tail" that raises the denaturation temperature necessary to amplify PCR product made using this primer.

Reactions 1-4 were made with solutions that were at ambient room temperature and included the three primers before temperature cycling was begun. Reactions 5-8 were made with the addition of the three primers postponed until these reactions were equilibrated to a temperature of 72° C. before beginning thermocycling. For this reason, reactions 5-8 are referred to as being given a "hot-start." Reactions 2-4 and 6-8 also contained a target, positive control DNA (purchased from PECI) containing HIV sequences to which RH171 (SEQ ID NO: 1), RH182 (SEQ ID NO: 3), and the 3' portion of RH176 (SEQ ID NO: 2) were homologous. This DNA was diluted such that each reaction containing it had, on average, four copies of the HIV sequence. Because the average number of copies is small, the actual number of copies in a given reaction can vary considerably. Since no HIV DNA target was added to reactions 1 and 5, these reactions served as negative controls.

All eight reactions were subjected to thermocycling using a Perkin Elmer Cetus DNA thermocycler as follows: denature at 96° C., hold for 1 minute, anneal at 64° C., hold for 1 minute. This profile was repeated for 29 cycles, during which the flanking primer pair, RH171 (SEQ ID NO: 1) and RH176 (SEQ ID NO: 2), efficiently annealed and were used in amplification, while the nested primer RH182 (SEQ ID NO: 3), which does not efficiently anneal at 64° C., was not used in efficient amplification. This was followed by denaturation at 96° C., hold for 1 minute, annealing at 52° C., hold for 1 minute. This profile was repeated for 2 cycles, during which all three primers efficiently annealed and were extended in amplification such that products were made using either RH171 (SEQ ID NO: 1) and RH176 (SEQ ID NO: 2), or RH171 (SEQ ID NO: 1) and RH182 (SEQ ID NO: 3). Because the use of a third, nested primer, increases product specificity, products made using RH171 (SEQ ID NO: 1) and RH182 (SEQ ID NO: 3) were more likely to be HIV specific. These cycles were followed by denaturation at 86° C., hold for 1 minute, anneal at 52° C., hold for 1 minute. This profile was repeated 18 times, during which, products that include the GC-rich primer RH176 (SEQ ID NO: 2), both HIV specific and non-specific, did not efficiently denature at 86° C. and, therefore, did not amplify efficiently, while the amplified HIV sequences made using the nested primer RH182 (SEQ ID NO: 3) and RH171 (SEQ ID NO: 1) did efficiently denature and amplify.

Figure 3:
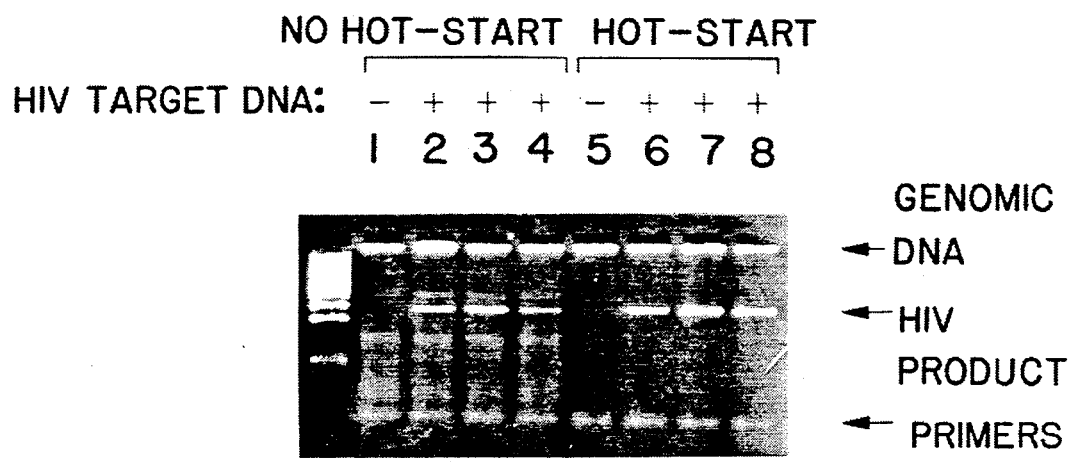
FIG. 3 provides the results of PCR amplification using the Drop-In/Drop-Out method for detecting HIV nucleic acids. The experiment is described at Example I.

All eight reactions were analyzed, when completed, by gel electrophoresis and photographed (see FIG. 3). Reactions 2-4 and 5-8 were shown to contain a product of the expected size (approximately 200 bp) as the predominant band on the gel. Reactions 1 and 5, the negative controls, contained no such product. However, reactions 2-4, which were not given a "hot-start," could be seen to contain DNA fragments of other than the expected size. These other DNA fragments were also visible in reaction 1, indicating that they are not derived from HIV sequences. These other DNA fragments were not visible in reactions 6-8, indicating that use of the "hot-start" had enhanced the specificity of these reactions.

Figure 4:
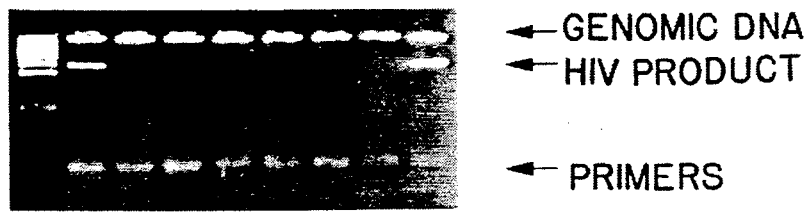
FIG. 4 provides the results of the Drop-in/Drop-out PCR method to detect a single copy of HIV DNA in a sample as described in EXAMPLE I.

Eight additional reactions were performed as described above, except that all were given a "hot-start" as described above. The positive control DNA was diluted in these eight reactions, numbered 1 through 8, such that on average, each contains half an HIV target molecule. Since a molecule cannot be divided, this means that some reactions should contain a target molecule and some should not. If this experiment were repeated many times, the fraction of reactions that do contain a target will vary considerably, but should be on average about half. Those that do contain a target molecule are most likely to contain a single target molecule. Upon completion of the reactions, all eight were analyzed by gel electrophoresis and photographed (see FIG. 4). The result was that two of the eight reactions, numbers 1 and 8, displayed a DNA fragment of the expected size (approximately 200 bp) as the predominant band on the gel, with no other bands that migrated into the gel visible except a band corresponding to the primers. Reactions 2-6 displayed no such bands nor any other DNA fragment bands due presumably to the absence of the specific HIV template sequence.

EXAMPLE II

Demonstration of Increased Specificity Via "Drop-in/Drop-out" Protocol

The experiment described in Example I was repeated in such a way as to demonstrate that the thermocycling parameters had the expected effect on amplification specificity.

Figure 5:
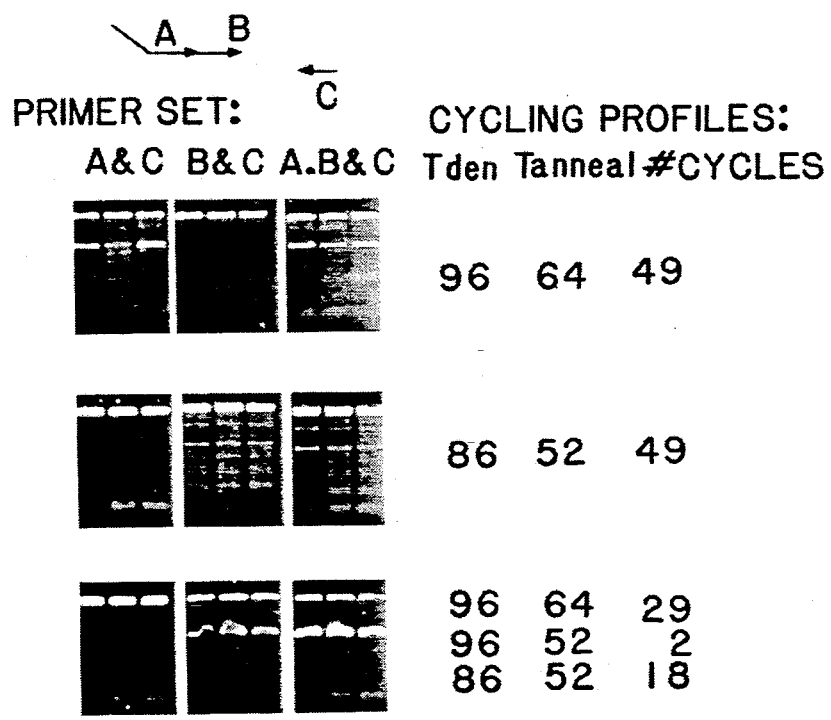
FIG. 5. demonstrates the increased specificity provided by the present methods and is described at Example II.

Nine reactions were set up as described in Example I, except that, on average, ~20 copies of HIV plasmid were present in each reaction mix and each reaction did not contain the nested primer RH182 (SEQ ID NO: 3). In FIG. 5, this primer is indicated as primer B, and the flanking primers RH176 (SEQ ID NO: 2) and RH171 (SEQ ID NO: 1), which were included in the reaction mixtures, are indicated as primer A and primer C, respectively. These nine reactions will be referred to here as "A and C" reactions. Nine other reactions were set up in the same way except containing primers RH182 (SEQ ID NO: 3) and RH171 (SEQ ID NO: 1) only. These reactions will be referred to, as "B and C" reactions.

Nine additional reactions were set up in the same way except using all three primers, RH176 (SEQ ID NO: 2), RH182 (SEQ ID NO: 3), and RH171 (SEQ ID NO: 1).

These reactions will be referred to as "A, B, and C" reactions.

All reactions were begun using a "hot-start" as described in Example I. Three reactions each of the "A and C," "B and C," and "A, B, and C" groups were amplified using conditions that prevented the "drop-in" primer "B" from priming DNA synthesis. These were amplified in a thermocycler using 49 cycles at a denaturation temperature of 96° C. and an annealing temperature of 64° C. This annealing temperature was above the calculated Tm of primer B (RH182 (SEQ ID NO: 3)). As expected, in the "B and C" group, in which primer B was the only "left" primer present, there was no detectable PCR product when aliquots of the three amplifications were run out on agarose gel electrophoresis as shown in FIG. 5. When A and C or A, B, and C were present, product was observed that was of the size expected for HIV sequences bound by primers A and C, as well as other, non-specific product.

Three reactions from each of the three groups were also amplified using conditions that prevented DNA synthesized from primer "A" (RH176 (SEQ ID NO: 2)), which contains the G-C rich, non-complementary, 5' "tail," from denaturing and amplifying. These conditions were a denaturation temperature of 86° C. and an annealing temperature of 52° C. for 49 cycles. This annealing temperature was low enough to allow annealing and extension of primer B (RH182 (SEQ ID NO: 3)). As expected, no amplification product was seen upon gel electrophoresis of the "A and C" reactions amplified under these conditions. However, amplification products of a size corresponding to HIV sequences bound by primers B and C, as well as many extra, non-specific DNA products, were seen in amplifications "B and C" and "A, B, and C" (see FIG. 5).

Figure 2:
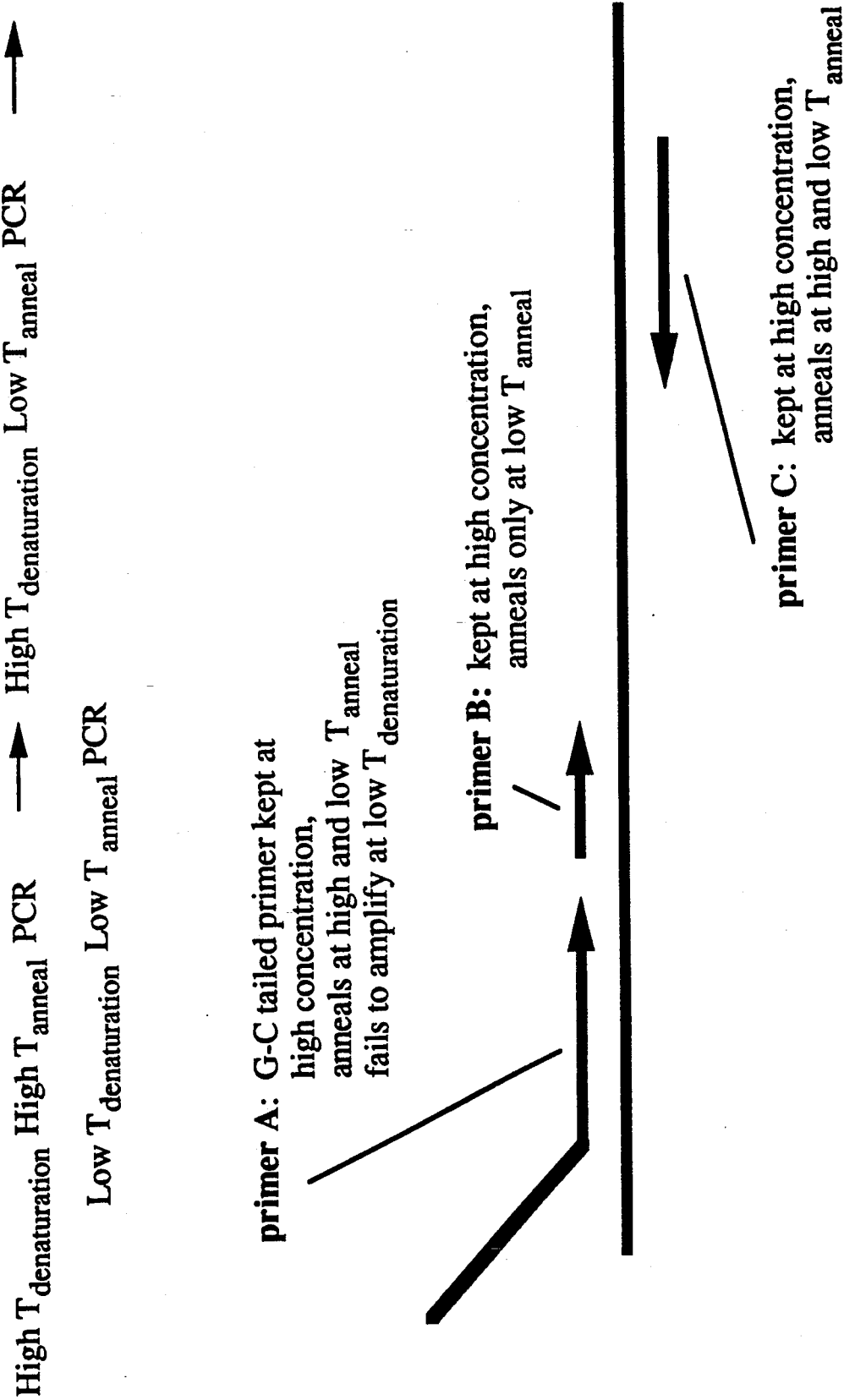
FIG. 2 provides a schematic description of the "Drop-In/Drop-Out" method demonstrated at Example I.

Finally, three reactions of each of the three groups were amplified under conditions that allowed "drop-in/drop-out" amplifications as diagrammed in FIG. 2. These conditions were 29 cycles using a 96° C. denaturation and a 64° C. annealing, two cycles using a 96° C. denaturation and a 52° C. annealing, and 18 cycles using 86° C. denaturation and 52° C. annealing. Only the first two thermocycling phrases allowed utilization of primer A as an efficient amplification primer; these 31 cycles were not enough to detectably amplify the few HIV target molecules present in the sample by gel electrophoresis and ethidium bromide staining. Consequently, as expected, no detectable PCR product was formed with primers A and C only. Also as predicted, the complete drop-in/drop-out protocol using all three primers gave the most specific amplification with the greatest yield of product (FIG. 5). The only other major band seen upon gel electrophoresis was attributable to the respectively long primer A (RH176 (SEQ ID NO: 2)).

Surprisingly, an increase in specificity and yield was also seen under these amplification conditions using only primers B and C. As discussed above, this was due to inefficient, yet highly specific, amplification during the 29 cycles at an annealing temperature greater than the Tm of primer B. The additional 20 cycles at the lower annealing temperature were sufficient to amplify this inefficiently, yet specifically, produced product.

---

SEQUENCE LISTING ( 1 ) GENERAL INFORMATION:

( i i i ) NUMBER OF SEQUENCES: 3

( 2 ) INFORMATION FOR SEQ ID NO: 1:

( i ) SEQUENCE CHARACTERISTICS:
( A ) LENGTH: 26 bases
( B ) TYPE: nucleic acid
( C ) STRANDEDNESS: single
( D ) TOPOLOGY: linear ( i i ) MOLECULE TYPE: Other Nucleic Acid ( x i ) SEQUENCE DESCRIPTION: SEQ ID NO: 1:

CCAGGCCAGA TGAGAGAACC AAGGGG                                           2 6

( 2 ) INFORMATION FOR SEQ ID NO: 2:

( i ) SEQUENCE CHARACTERISTICS:
( A ) LENGTH: 52 bases
( B ) TYPE: nucleic acid
( C ) STRANDEDNESS: single
( D ) TOPOLOGY: linear ( i i ) MOLECULE TYPE: Other Nucleic Acid ( x i ) SEQUENCE DESCRIPTION: SEQ ID NO: 2:

GCGGGCAGGG CGGCGGGGGC GGGGCCGAAC CGGTCTACAT AGTCTCTAAA GG              5 2

( 2 ) INFORMATION FOR SEQ ID NO: 3:

( i ) SEQUENCE CHARACTERISTICS:
( A ) LENGTH: 17 bases
( B ) TYPE: nucleic acid

-continued ( C ) STRANDEDNESS: single
( D ) TOPOLOGY: linear ( i i ) MOLECULE TYPE: Other Nucleic Acid ( x i ) SEQUENCE DESCRIPTION: SEQ ID NO: 3:

GGTCCCTGTC TTATGTC                 17

Although the foregoing invention has been described in some detail for the purpose of illustration, it will be obvious that changes and modification are practical within the scope of the appended claims by those of ordinary skill in the art.

We claim:

1. A method for nested amplification of a sequence within a target nucleic acid in a sample, the method comprises:
   (a) simultaneously mixing said sample in an amplification reaction mixture containing an outer primer pair and an inner primer pair, wherein said outer primer pair is capable of amplifying a target nucleic acid to provide an amplified target sequence, and said inner primer pair is capable of amplifying a subsequence within said target sequence;
   (b) treating the amplification reaction mixture of step (a) in an amplification reaction at a temperature for annealing and extending said outer primer pair on said target nucleic acid and at a temperature for denaturing the extension products of said outer primer pair to provide an amplified target sequence, wherein said temperature for annealing and extending said outer primer pair is higher than the temperature for annealing and extending said inner primer pair to said target nucleic acid and said temperature does not allow efficient extension of at least one member of said inner primer pair; and
   (c) treating the mixture of step (b) in an amplification reaction at said temperature for annealing and extending said inner primer pair on said amplified target sequence, and at an temperature for denaturing the extension products of said inner primer pair to provide an amplified subsequence.

2. The method of claim 1 wherein said amplification reaction mixture contains three primers, wherein first primer is a member of said outer primer pair, the second primer is a member of said outer primer pair and said inner primer pair, and the third primer is a member of said inner primer pair.

3. The method of claim 2 wherein after step (b) said temperature for annealing and extending said outer primer pair is lowered to provide said temperature for annealing and extending said inner primer pair at step (c).

4. The method of claim 3 wherein said temperature of annealing and extending said inner primer pair is between 1° C. and 30° C. lower than said appropriate temperature for annealing and extending said outer primer pair.

5. The method of claim 4 wherein at step (a) said first primer is present in said amplification reaction mixture at a limiting concentration.

6. The method of claim 5 wherein said limiting concentration is between 1% and 50% of the concentration of said second and third primers in said amplification reaction mixture.

7. The method of claim 4 wherein at step (c) said temperature for denaturing the extension products of said inner primer pair is suitable for denaturing the extension products of said outer primer pair and the method further comprises:
   (d) amplifying said subsequence, at an appropriate temperature for annealing and extending said inner primer pair on said amplified target sequence, and at a temperature for denaturing only the extension products of said inner primer pair to provide an amplified subsequence, wherein said temperature for denaturing only the extension products of said inner primer pair is lower than said temperature for denaturing the extension products of said outer primer pair.

8. The method of claim 7 wherein at step (d) the temperature for denaturing only the extension products of said inner primer pair is from 1° C. to 20° C. lower than the temperature for denaturing the extension products of said outer primer pair.

9. The method of claim 7 wherein said first primer comprises a 5' G-C tail.

10. The method of claim 1 that comprises: (d) determining if amplification has occurred.

11. The method of claim 10 wherein said amplification reaction mixture further comprises a detectable DNA binding agent.

12. The method of claim 11 wherein said binding agent is ethidium bromide.

13. The method of claim 11 that comprises, after step (b) and prior to step (c), determining if amplification has occurred.

14. The method of claim 1 wherein said target nucleic acid is an infectious agent.

15. The method of claim 1 wherein said target nucleic acid present at one copy per 70,000 cells.

16. The method of claim 1 wherein said target nucleic acid is a genetic marker and said outer primer pair hybridizes to a sequence known to be present.

17. The method of claim 16 wherein said inner primer pair hybridizes to an allele-specific sequence.

18. The method of claim 17 wherein said allele-specific sequence is indicative of a particular disease state or useful for tissue or blood typing.

* * * * *